(12) United States Patent
Matsui et al.

(10) Patent No.: US 8,403,827 B2
(45) Date of Patent: Mar. 26, 2013

(54) ENDOSCOPIC INSERTION AID, ENDOSCOPIC SYSTEM, AND METHOD OF INSERTING INSERTION PORTION OF ENDOSCOPE INTO BODY CAVITY BY USE OF ENDOSCOPIC INSERTION AID

(75) Inventors: Raifu Matsui, Hino (JP); Nobuyuki Matsuura, Hino (JP); Seisuke Takase, Hachioji (JP); Hidenobu Kimura, Hachioji (JP); Takatoshi Yoshida, Hachioji (JP)

(73) Assignee: Olympus Medical Systems Corp. (JP)

( * ) Notice: Subject to any disclaimer, the term of this patent is extended or adjusted under 35 U.S.C. 154(b) by 985 days.

(21) Appl. No.: 11/779,601

(22) Filed: Jul. 18, 2007

(65) Prior Publication Data
US 2008/0033246 A1 Feb. 7, 2008

(30) Foreign Application Priority Data
Aug. 1, 2006 (JP) .................. 2006-210066

(51) Int. Cl.
*A61B 1/00* (2006.01)
(52) U.S. Cl. .................. 600/115; 600/114; 600/116
(58) Field of Classification Search .................. 600/104, 600/106, 114–116; 604/95.03, 96.01, 97.01, 604/99.01, 101.01–101.05, 103.06–103.08; 606/191–200
See application file for complete search history.

(56) References Cited

U.S. PATENT DOCUMENTS

| | | | |
|---|---|---|---|
| 5,738,629 A | 4/1998 | Moll et al. | |
| 2002/0143237 A1* | 10/2002 | Oneda et al. | 600/116 |
| 2005/0080313 A1* | 4/2005 | Stewart et al. | 600/3 |
| 2005/0159645 A1* | 7/2005 | Bertolero et al. | 600/116 |
| 2006/0100480 A1* | 5/2006 | Ewers et al. | 600/114 |

FOREIGN PATENT DOCUMENTS

| | | |
|---|---|---|
| JP | 04-297219 | 10/1992 |
| JP | 05-063550 | 3/1993 |
| JP | 07-265411 | 10/1995 |
| JP | 10-155733 | 6/1998 |
| JP | 2003-088495 | 3/2003 |
| JP | 2005-515797 | 6/2005 |

(Continued)

OTHER PUBLICATIONS

European Search Report dated Dec. 27, 2007 issued in corresponding European Application No. EP 07 01 4085.
Letter from Associates reporting the European Search Report dated Jan. 21, 2008.

(Continued)

*Primary Examiner* — Matthew J Kasztejna
*Assistant Examiner* — Ryan Henderson
(74) *Attorney, Agent, or Firm* — Ostrolenk Faber LLP

(57) ABSTRACT

An endoscopic insertion aid includes a tube member, a pipeline and a plurality of balloons. The tube member allows an insertion section of an endoscope to be inserted therethrough, and guides the longitudinal movement of the insertion section. The pipeline is provided in the tube member, and communicates with a supply/discharge unit to supply a fluid to or discharge the fluid from the distal end of the tube member. The balloons are disposed on the outer periphery of the distal end of the tube member longitudinally along the tube member, communicate with the pipeline, and inflate/deflate in accordance with the supply/discharge of the fluid via the pipeline. The balloon disposed on the distal side of the tube member is inflated to have an outside diameter larger than that of the balloon disposed closer to the proximal side than the balloon disposed on the distal side when the balloons are inflated.

2 Claims, 5 Drawing Sheets

FOREIGN PATENT DOCUMENTS

| | | |
|---|---|---|
| WO | WO 95/32011 | 11/1995 |
| WO | WO 03/080155 | 10/2003 |

OTHER PUBLICATIONS

Anonymous: "Variably inflatable balloon catheter for even delivery of stents" Research Disclosure, Mason Publications, Hampshire, GB, vol. 455, No. 61, Mar. 2002, XP007129996 ISSN: 0374-4353.

Letter from German associate dated Jun. 16, 2009 forwarding the Search Report dated May 18, 2009 to Japanese associate, including discussion of relevancy thereof.

Search Report issued by European Patent Office in connection with corresponding application No. EP 07 014 085.0 on May 18, 2009.

Office Action issued by the Japanese Patent Office on Sep. 27, 2011 in connection with corresponding Japanese Patent Application No. 2006-210066.

Translation of Office Action issued by the Japanese Patent Office on Sep. 27, 2011 in connection with corresponding Japanese Patent Application No. 2006-210066.

* cited by examiner

US 8,403,827 B2

ENDOSCOPIC INSERTION AID, ENDOSCOPIC SYSTEM, AND METHOD OF INSERTING INSERTION PORTION OF ENDOSCOPE INTO BODY CAVITY BY USE OF ENDOSCOPIC INSERTION AID

CROSS-REFERENCE TO RELATED APPLICATIONS

This application is based upon and claims the benefit of priority from prior Japanese Patent Application No. 2006-210066, filed Aug. 1, 2006, the entire contents of which are incorporated herein by reference.

BACKGROUND OF THE INVENTION

1. Field of the Invention

This invention relates to an endoscopic insertion aid for facilitating insertion by aiding in the insertion of an insertion section of an endoscope into a region such as the large intestine where insertion is difficult, an endoscopic system, and a method of inserting the insertion section of the endoscope into a body cavity by use of the endoscopic insertion aid.

2. Description of the Related Art

For example, an endoscopic insertion aid having a plurality of balloons at its distal end is disclosed in Jpn. Pat. Appln. KOKAI Publication No. 10-155733. In this endoscopic insertion aid, the inner wall of a body cavity is expanded outward by the balloons to pull the aid to a hand side so that the aid is fixed to the inner wall of the body cavity. Then, for example, bent parts or twisted parts of the intestinal wall become substantially straight, thereby permitting the improvement of the insertability of an insertion section.

BRIEF SUMMARY OF THE INVENTION

An endoscopic insertion aid according to this invention includes: a tube member, a pipeline and a plurality of balloons. The tube member allows an insertion section of an endoscope to be inserted therethrough, and guides the longitudinal movement of the insertion section. The pipeline is provided in the tube member, and communicates with a supply/discharge unit to supply a fluid to the distal end of the tube member or discharge the fluid from the distal end of the tube member. The plurality of balloons are disposed on the outer periphery of the distal end of the tube member longitudinally along the tube member, communicate with the pipeline, and inflate/deflate in accordance with the supply/discharge of the fluid via the pipeline. The balloon disposed on the distal side of the tube member is inflated to have an outside diameter larger than that of the balloon disposed closer to the proximal side of the tube member than the balloon disposed on the distal side when the plurality of balloons are inflated.

An endoscopic insertion aid according to this invention includes: a tube member, a pipeline, a plurality of balloons and regulating means. The tube member allows an insertion section of an endoscope to be inserted therethrough, and guides the longitudinal movement of the insertion section. The pipeline is provided in the tube member, and communicates with a supply/discharge unit to supply a fluid to the distal end of the tube member or discharge the fluid from the distal end of the tube member. The plurality of balloons are disposed at the distal end of the tube member longitudinally along the tube member, communicate with the pipeline, and inflate/deflate in accordance with the supply/discharge of the fluid via the pipeline. The regulating means operates so that the balloon disposed on the distal side of the tube member is inflated to have an outside diameter larger than that of the balloon disposed closer to the proximal side of the tube member than the balloon disposed on the distal side when the plurality of balloons are inflated.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

A best mode of carrying out this invention will hereinafter be described with reference to the drawings.

A first embodiment will be described using FIGS. 1 to 4D.

Figure 1:
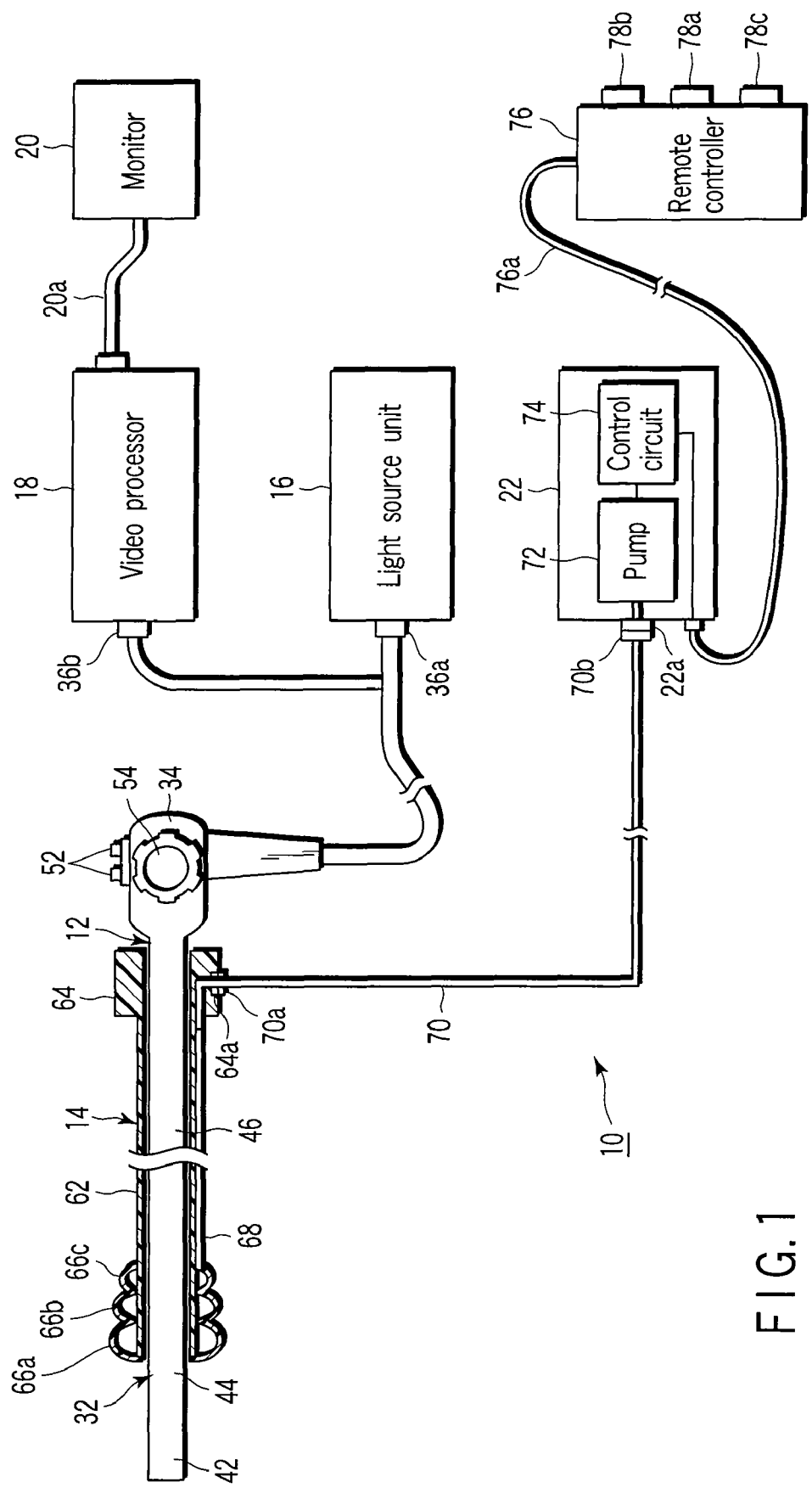
FIG. 1 is a schematic diagram showing an endoscopic system according to a first embodiment of the present invention.

As shown in FIG. 1, an endoscopic system 10 includes an endoscope 12, an overtube (insertion aid) 14, a light source unit 16, a video processor 18, a monitor 20, and a balloon control unit (supply/discharge unit) 22.

The endoscope 12 includes an elongate insertion section 32, and an operation section 34 provided at the proximal end of the insertion section 32, and a universal cord 36 extending from the operation section 34. The light source unit 16 is optically connected to a connector 36a at the end of the universal cord 36. Light emitted from the light source unit 16 exits from the distal end of the insertion section 32 via the universal cord 36, the operation section 34 and the insertion section 32. The video processor 18 is further electrically connected to a connector 36b at the end of the universal cord 36 extending in addition to the above-mentioned connector 36a. The monitor 20 is electrically connected to the video processor 18 via a cable 20a. Thus, when an optical image of a specimen is picked up by a solid-state image sensing device such as a CCD described later, its signal is processed by the video processor 18, and the image of the specimen picked up is displayed on the monitor 20.

The insertion section 32 includes a rigid distal portion 42, a bending portion 44 capable of vertically and horizontally bending, and a long and flexible tube portion 46.

The rigid distal portion 42 is disposed at a most distal position of the insertion section 32. The rigid distal portion 42 is provided with a forceps opening communicating with an illumination optical system, an observation optical system such as the solid-state image sensing device, and a treatment tool insertion channel, and also provided with a nozzle for supplying air into a body cavity and water to an observation lens (neither the forceps opening nor the nozzle is shown). The treatment tool insertion channel communicates with a treatment tool insertion hole (not shown) of the operation section 34.

The distal end of the bending portion 44 is coupled to the proximal end of the rigid distal portion 42. The distal end of the flexible tube portion 46 is coupled to the proximal end of the bending portion 44. The distal end of the operation section 34 is coupled to the proximal end of the flexible tube portion 46. That is, the distal end of the operation section 34 is coupled to the proximal end of the insertion section 32.

The operation section 34 is provided with a remote switch 52 for the remote control of the video processor 18, etc., and a bending operation knob 54 rotated by an operator. When the bending operation knob 54 is operated, the above-mentioned bending portion 44 of the insertion section 32 curves in directions to deviate from the longitudinal axis of the flexible tube portion 46, for example, vertically and horizontally.

Figure 2:
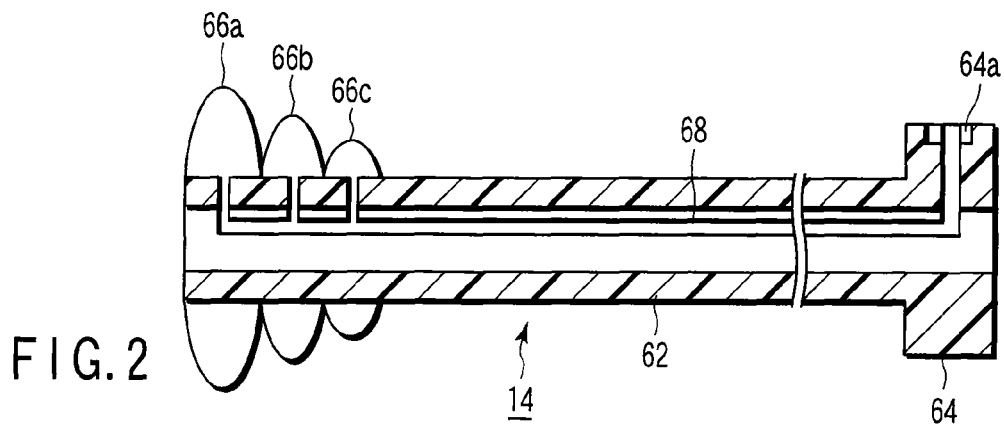
FIG. 2 is a schematic longitudinal sectional view showing an overtube in the endoscopic system according to the first embodiment.

As shown in FIG. 2, the overtube 14 includes a main body (tube member) 62 disposed to cover the outer periphery of the insertion section 32 of the endoscope 12, a grip 64 provided at the proximal end of the main body 62, and first to third balloons 66a, 66b and 66c provided on the outer peripheral surface of the distal end of the main body 62. In the main body 62 and the grip 64, a balloon communication pipeline 68 is formed which communicates with the first to third balloons 66a, 66b and 66c. The distal end of the balloon communication pipeline 68 communicates with the first to third balloons 66a, 66b and 66c. The proximal end of the balloon communication pipeline 68 communicates with a connector 64a provided in the grip 64.

A connection pipeline 70 is disposed between the overtube 14 and the balloon control unit 22. Connectors 70a and 70b are provided at one end and the other end of the connection pipeline 70, respectively. The connector 70a at one end of the connection pipeline 70 is connected to the connector 64a of the grip 64. The connector 70b at the other end of the connection pipeline 70 is connected to a connector 22a of the balloon control unit 22.

The balloon control unit 22 includes a pump 72 capable of supplying/discharging (sucking) a gas, a control circuit 74 for controlling the pump 72, and a remote controller 76 electrically connected to the control circuit 74 via a connection cable 76a. This remote controller 76 is provided with a stop button 78a, a pressurization button 78b and a decompression button 78c. When the stop button 78a is depressed, its signal is input to the control circuit 74. Then, the control circuit 74 stops the operation of the pump 72. When the pressurization button 78b is depressed, its signal is input to the control circuit 74. Then, the control circuit 74 operates the pump 72 so that the gas is supplied from the connection pipeline 70 to the balloon communication pipeline 68 of the overtube 14. When the decompression button 78c is depressed, its signal is input to the control circuit 74. Then, the control circuit 74 operates the pump 72 so that the gas is discharged from the connection pipeline 70 and the balloon communication pipeline 68 of the overtube 14.

As shown in FIGS. 1 and 2, for example, the three first to third balloons 66a, 66b and 66c are disposed at the distal end of the overtube 14. The balloons 66a, 66b and 66c are formed of, for example, silicone rubber, latex rubber, or an elastic elastomer. The balloons 66a, 66b and 66c communicate with each other through the balloon communication pipeline 68 provided in the main body 62. Further, the outside diameter of the first balloon 66a on the most distal side when inflated is formed to be greater than the outside diameter of the adjacent second balloon 66b when inflated. Moreover, the outside diameter of the third balloon 66c adjacent to the second balloon 66b is formed to be smaller than that of the second balloon 66b when the second and third balloons 66b and 66c are inflated.

It is to be noted that the balloons 66a, 66b and 66c are formed of, for example, one cylindrical member. The distal end and proximal end of this cylindrical member are fixed by being wound and bound with, for example, threads 80 (see FIG. 7). Then, the cylindrical member is wound and bound with the threads 80 at appropriate two places so that the first to third balloons 66a, 66b and 66c are formed. Further, an adhesive is applied to the parts wound with the threads 80 for fixture. Thus, the first to third balloons 66a, 66b and 66c are formed.

Next, the function of the endoscopic system 10 according to this embodiment will be described using FIGS. 3A to 4D.

Figure 3A:
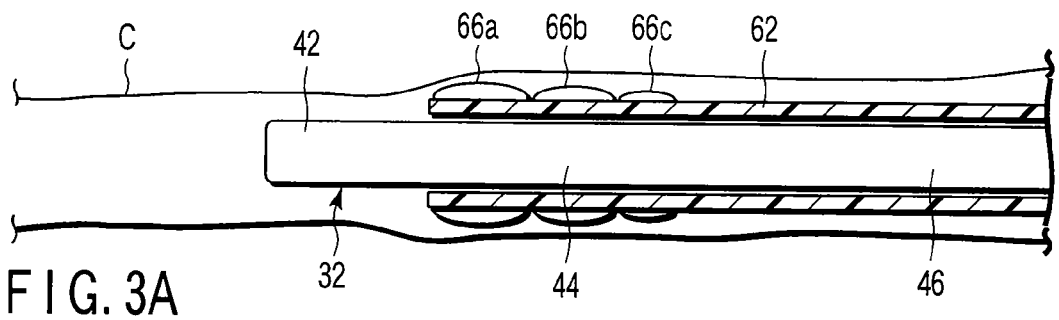
FIGS. 3A to 3D are schematic diagrams showing a procedure for inserting an insertion section of an endoscope into the large intestine by use of the endoscopic system according to the first embodiment.

The insertion section 32 of the endoscope 12 is per anum inserted into the large intestine C shown in FIG. 3A, and the main body 62 of the overtube 14 is inserted.

Figure 3B:
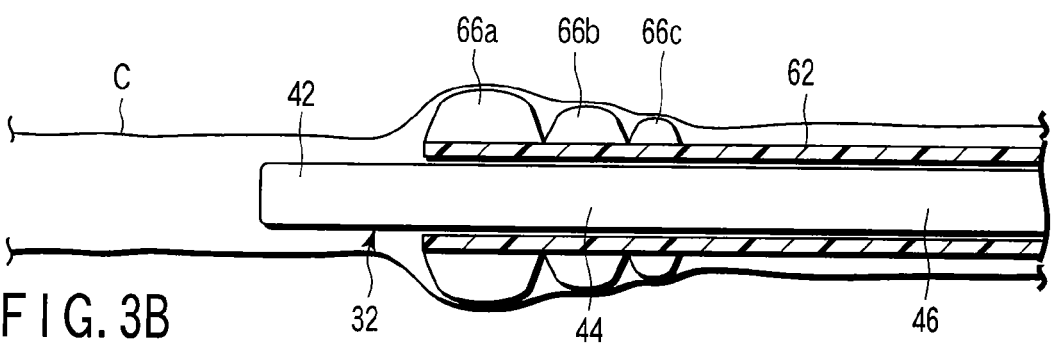

As shown in FIG. 3B, the pressurization button 78b of the remote controller 76 is depressed. A signal is input from the remote controller 76 to the control circuit 74 via the connection cable 76a. The control circuit 74 operates the pump 72 while controlling the pump 72. Then, the balloons 66a, 66b and 66c of the overtube 14 are inflated so that the intestinal wall is expanded outward by the balloons 66a, 66b and 66c. At this point, for example, the pump 72 is controlled by the control circuit 74 to adjust the velocity and amount of a fluid (gas), thereby slowly inflating the balloons 66a, 66b and 66c. Thus, the balloons 66a, 66b and 66c slowly expand the intestinal wall outward. Further, the position of the overtube 14 is held to the large intestine C by frictional force between the balloons 66a, 66b and 66c and the inner wall of the intestine.

It is to be noted that the pressurization of the balloons 66a, 66b and 66c is automatically stopped when specified pressure is reached. Alternatively, the stop button 78a is depressed and its signal is input to the control circuit 74 before the specified pressure is reached. The control circuit 74 stops the operation of the pump 72.

Figure 3C:
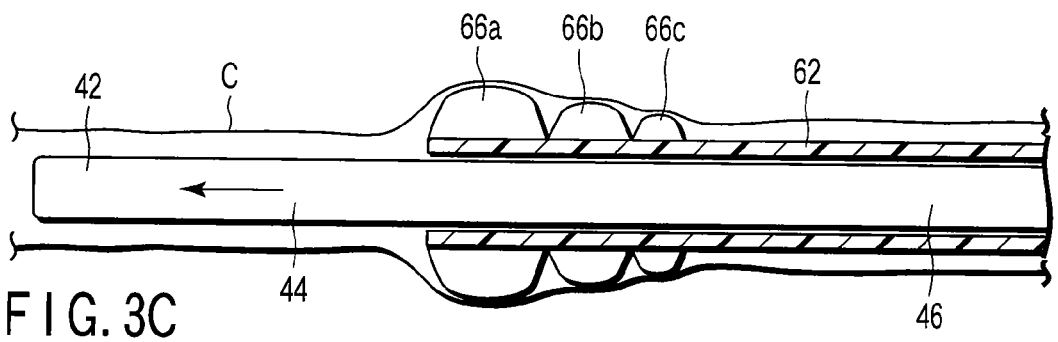

When the balloons 66a, 66b and 66c of the overtube 14 are inflated as shown in FIG. 3B, the intestinal wall is expanded outward so that the distal side of the first balloon 66a is also expanded. Thus, as shown in FIG. 3C, the insertion section 32 of the endoscope 12 is moved to the inner side of the large intestine C while the position of the overtube 14 is being held. At this point, the bending portion 44 of the insertion section 32 is caused to further project forward from the distal end of the main body 62 of the overtube 14.

Figure 3D:
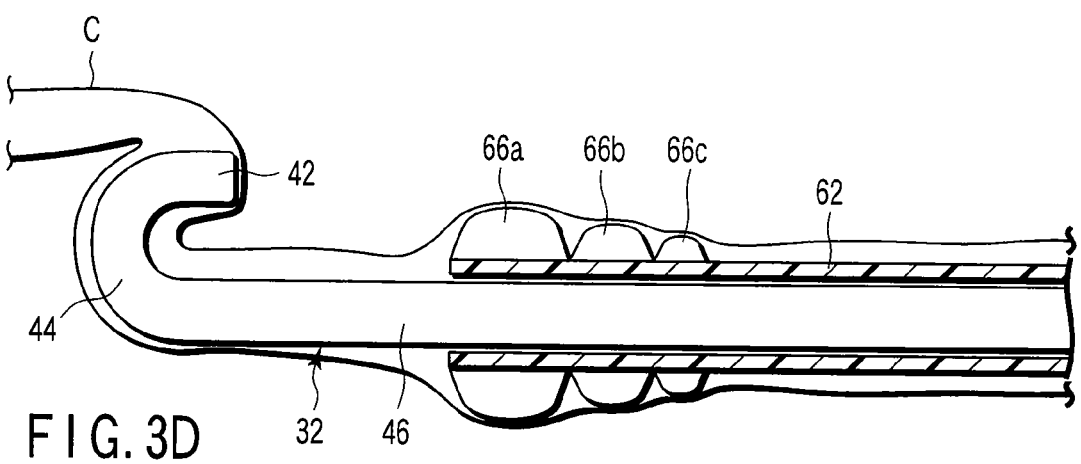

Then, the bending operation knob 54 of the operation section 34 is operated to curve the bending portion 44 of the insertion section 32, as shown in FIG. 3D. Thus, the large intestine C deforms in an S-shape. Therefore, the large intestine C is held so that it is substantially caught between the bending portion 44 of the insertion section 32 of the endoscope 12 and the rigid distal portion 42.

Figure 4A:
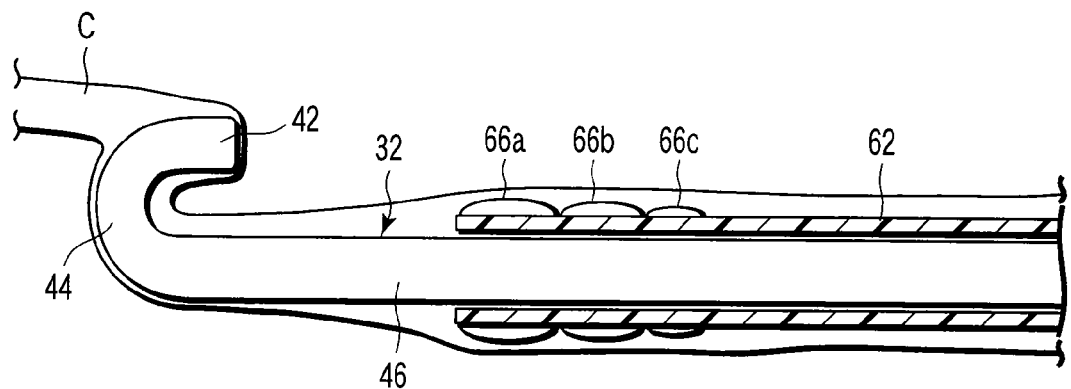
FIGS. 4A to 4D are schematic diagrams showing a procedure for inserting the insertion section of the endoscope into the large intestine by use of the endoscopic system according to the first embodiment.

The decompression button 78c of the remote controller 76 is operated to operate the pump 72, and the balloons 66a, 66b and 66c of the overtube 14 are deflated, as shown in FIG. 4A. At this point, the pump 72 is controlled by the control circuit 74 to discharge the gas from the balloons 66a, 66b and 66c as fast as possible. Then, it is possible to quickly move on to the next operation.

Figure 4B:
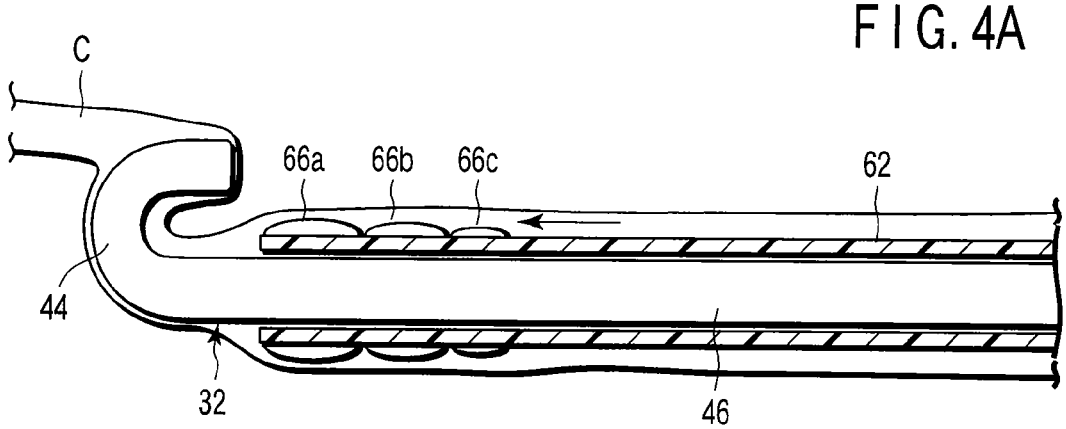

As shown in FIG. 4B, the overtube 14 is moved to the inner side along the insertion section 32 of the endoscope 12.

Figure 4C:
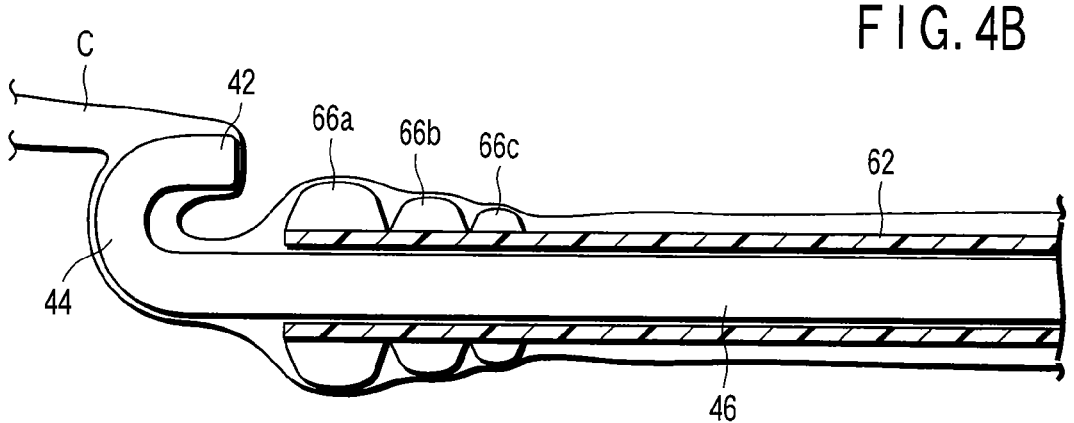

As shown in FIG. 4C, the balloons 66a, 66b and 66c of the overtube 14 are inflated to expand the wall of the large intestine C. In this case as well, the balloons 66a, 66b and 66c are slowly inflated. Then, the position of the overtube 14 is fixed by the balloons 66a, 66b and 66c.

Figure 4D:
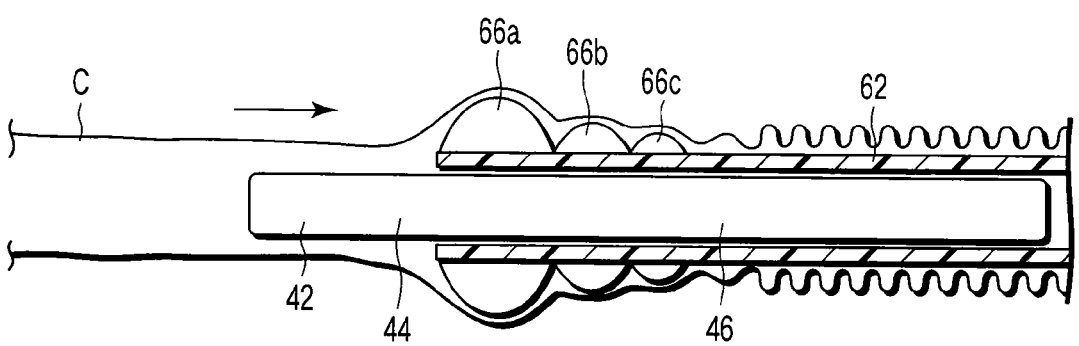

As shown in FIG. 4D, the bending operation knob 54 of the operation section 34 of the endoscope 12 is operated to make the curved bending portion 44 of the insertion section 32 straight. That is, the holding of the large intestine C by the bending portion 44 of the insertion section 32 and the rigid distal portion 42 is released. Further, the overtube 14 and the insertion section 32 of the endoscope 12 are pulled together so that their relative movement is prevented. Then, using the balloons 66a, 66b and 66c in which the diameter is larger on the distal side and smaller on the proximal side, the large intestine C is pushed out to the hand side (anal side) by the proximal part of the third balloon 66c. In the same manner, the large intestine C is pushed out to the hand side by the proximal part of the second balloon 66b. Further, the large intestine C is pushed out to the hand side by the proximal part of the third balloon 66c. Then, the folds of the inner wall of the large intestine C are hooked between the first balloon 66a and the second balloon 66b, between the second balloon 66b and the third balloon 66c and by the proximal part of the third balloon 66c. Therefore, when the overtube 14 and the insertion section 32 of the endoscope 12 are pulled together, the large intestine C is pulled to the hand side and efficiently folded (shortened) because the folds of the large intestine C are hooked by the balloons 66a, 66b and 66c.

Furthermore, as shown in FIG. 3C, the insertion section 32 of the endoscope 12 is inserted into the inner side with respect to the overtube 14. Subsequently, similar operation is carried out to insert the distal end of the insertion section 32 into the inner side of the large intestine C.

As described above, the following effects can be obtained according to this embodiment.

The plurality of balloons 66a, 66b and 66c are provided at the distal end of the overtube 14. Moreover, the diameter of the first balloon 66a is larger than the diameter of the second balloon 66b, and the diameter of the second balloon 66b is larger than the diameter of the third balloon 66c. Thus, the effect of hooking the inner wall of the large intestine C with the balloons 66a, 66b and 66c can be increased when the large intestine C is folded onto the anal side. Further, the area of contact with the intestinal wall in folding the large intestine C can be large. Thus, the force of fixing the balloons 66a, 66b and 66c to the wall of the large intestine C can be increased.

In addition, while the use of the three balloons 66a, 66b and 66c has been described in this embodiment, for example, two or four balloons may also be used, and the suitable number of balloons is selected.

Next, a second embodiment will be described using FIG. 5. This embodiment is a modification of the first embodiment, so that the same signs are assigned to the same members as those described in the first embodiment, and these members are not described in detail.

First to third balloons 66a, 66b and 66c are formed into, for example, separate members, but are formed of the same material at about the same thickness.

Figure 5:
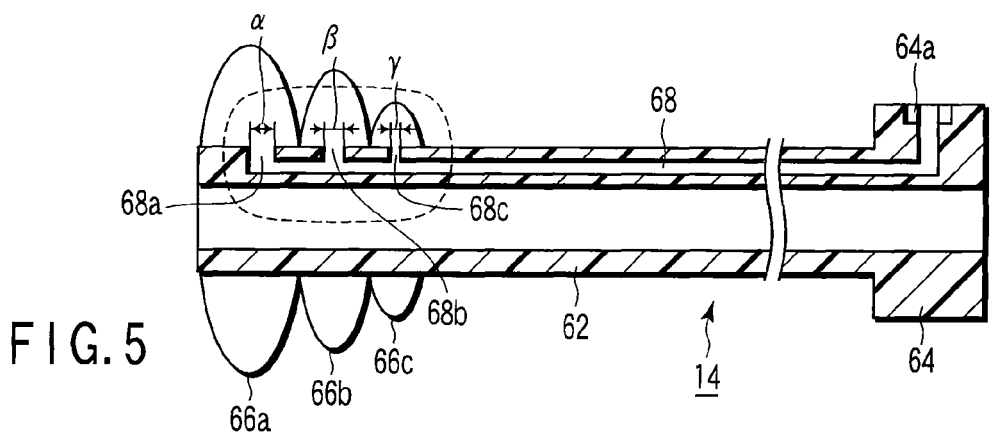
FIG. 5 is a schematic longitudinal sectional view showing an overtube in an endoscopic system according to a second embodiment of the present invention.

As shown in FIG. 5, balloon communication holes 68a, 68b and 68c of the balloons 66a, 66b and 66c communicating with a balloon communication pipeline 68 have cross-sectional areas different from each other. The cross-sectional area α of the first balloon communication hole 68a providing communication between the first balloon 66a and the balloon communication pipeline 68 is formed to be the largest. The cross-sectional area β of the second balloon communication hole 68b providing communication between the second balloon 66b and the balloon communication pipeline 68 is formed to be smaller than that of the first balloon communication hole 68a. The cross-sectional area γ of the third balloon communication hole 68c providing communication between the third balloon 66c and the balloon communication pipeline 68 is formed to be smaller than that of the second balloon communication hole 68b.

Thus, when a gas is introduced through the balloon communication pipeline 68, the amount of gas flowing from the second balloon communication hole 68b into the second balloon 66b is greater than the amount of gas flowing from the third balloon communication hole 68c into the third balloon 66c. Moreover, the amount of gas flowing from the first balloon communication hole 68a into the first balloon 66a is greater than the amount of gas flowing from the second balloon communication hole 68b into the second balloon 66b.

Therefore, the times for inflating the first to third balloons 66a, 66b and 66c can be about the same. Then, it is possible to prevent, for example, any one of the first to third balloons 66a, 66b and 66c from being in an overpressurized state or a low pressure state.

Furthermore, the inflation amounts of the balloons 66a, 66b and 66c can be regulated by the cross-sectional areas α, β and γ of the balloon communication holes 68a, 68b and 68c. That is, the relationships between the cross-sectional areas α, β and γ of the first to third balloon communication holes 68a, 68b and 68c serve as means for regulating the inflation amounts of the balloons 66a, 66b and 66c so that one supply of gas causes the first balloon 66a to be inflated to the largest outside diameter, the second balloon 66b to be inflated to the second largest outside diameter, and the third balloon 66c to be inflated to the third largest outside diameter.

Next, a third embodiment will be described using FIGS. 6 and 7. This embodiment is a modification of the first embodiment, so that the same signs are assigned to the same members as those described in the first embodiment, and these members are not described in detail.

Figure 6:
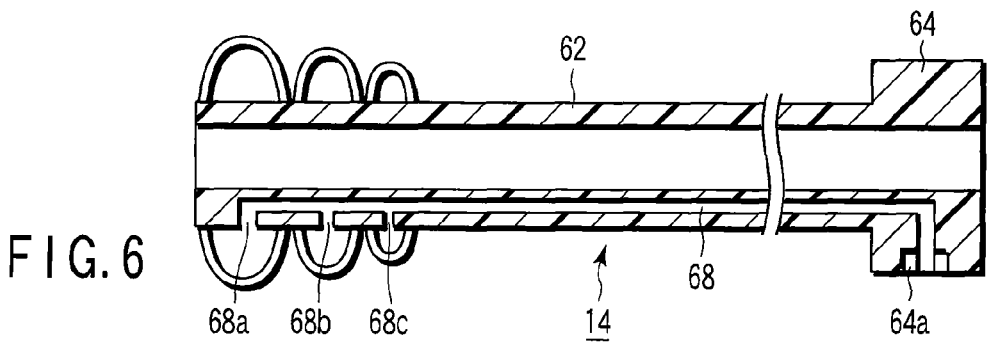
FIG. 6 is a schematic longitudinal sectional view showing an overtube in an endoscopic system according to a third embodiment of the present invention.
Figure 7:
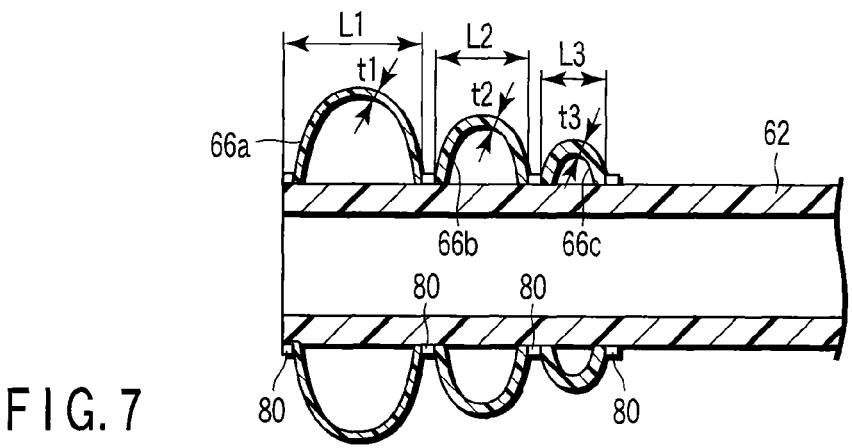
FIG. 7 is a schematic longitudinal sectional view showing the distal end of the overtube in the endoscopic system according to the third embodiment of the present invention.

FIG. 7 shows first to third balloons 66a, 66b and 66c in a magnified manner so that an overtube 14 shown in FIG. 6 is rotated 90 degrees around the axis of a main body 62.

As shown in FIG. 7, the length $L_1$ from the distal end to proximal end of the first balloon 66a is formed to be larger than the length $L_2$ from the distal end to proximal end of the second balloon 66b. Further, the length $L_2$ from the distal end to proximal end of the second balloon 66b is formed to be larger than the length $L_3$ from the distal end to proximal end of the third balloon 66c.

The length $L_1$ from the distal end to proximal end of the first balloon 66a is larger than the length $L_2$ from the distal end to proximal end of the second balloon 66b, such that the space in the first balloon 66a can be larger. Thus, a greater amount of fluid can be made to flow into the first balloon 66a than into the second balloon 66b. Then, the outside diameter of the first balloon 66a on the distal side can be larger than that of the second balloon 66b on the proximal side. The same applies to the relationship between the second balloon 66b and the third balloon 66c.

Thus, the inflation amounts of the balloons 66a, 66b and 66c can be regulated by the relationships between the lengths $L_1$, $L_2$ and $L_3$. That is, the relationships between the lengths $L_1$, $L_2$ and $L_3$ of the first to third balloons 66a, 66b and 66c serve as means for regulating the inflation amounts of the balloons 66a, 66b and 66c so that one supply of gas causes the first balloon 66a to be inflated to the largest outside diameter, the second balloon 66b to be inflated to the second largest outside diameter, and the third balloon 66c to be inflated to the third largest outside diameter.

Furthermore, the first to third balloons 66a, 66b and 66c are formed of the same material but are different from each other in thickness. The thickness $t_1$ of the first balloon 66a is formed to be smaller than the thickness $t_2$ of the second balloon 66b. The thickness $t_2$ of the second balloon 66b is formed to be smaller than the thickness $t_3$ of the third balloon 66c.

Therefore, the times for inflating the first to third balloons 66a, 66b and 66c can be about the same. Then, it is possible to prevent, for example, any one of the first to third balloons 66a, 66b and 66c from being in an overpressurized state or a low pressure state.

The first to third balloons 66a, 66b and 66c are formed of the same material, and the thickness $t_1$ of the first balloon 66a is formed to be smaller than the thickness $t_2$ of the second balloon 66b, and the thickness $t_2$ of the second balloon 66b is formed to be smaller than the thickness $t_3$ of the third balloon 66c. Thus, the inflation amounts of the balloons 66a, 66b and 66c can be regulated by the relationships between the thicknesses $t_1$, $t_2$ and $t_3$. That is, the relationships between the thicknesses $t_1$, $t_2$ and $t_3$ of the first to third balloons 66a, 66b and 66c serve as means for regulating the inflation amounts of the balloons 66a, 66b and 66c so that one supply of gas causes the first balloon 66a to be inflated to the largest outside diameter, the second balloon 66b to be inflated to the second largest outside diameter, and the third balloon 66c to be inflated to the third largest outside diameter.

In addition, the same material is used and thickness is varied in the first to third balloons 66a, 66b and 66c so that their inflation times may be substantially equal to each other in this embodiment described above. However, the inflation times of the balloons 66a, 66b and 66c can also be made substantially equal to each other by setting these balloons at a substantially uniform thickness but using materials of different expansion rates (the first balloon 66a has the highest expansion rate and the third balloon 66c has the lowest expansion rate). In this case, the cross-sectional areas of the first to third balloon communication holes 68a, 68b and 68c shown in FIG. 6 may be the same or different from each other. The cross-sectional areas are properly set in relation to the thickness and the material.

Furthermore, the first to third balloons 66a, 66b and 66c can also be formed of one cylindrical member. This cylindrical member is formed so that the thickness becomes linearly greater from the distal side to the proximal side. Then, when the cylindrical member is fixed by threads 80 at appropriate positions, the positions of the balloons 66a, 66b and 66c are regulated. At this point, the outside diameters of the first to third balloons 66a, 66b and 66c can also be about the same when the balloons 66a, 66b and 66c are in a deflated state. In this case, the first to third balloons 66a, 66b and 66c are inflated when the cross-sectional areas of the first to third balloon communication holes 68a, 68b and 68c are the same. Then, the first balloon 66a is inflated into the largest size and the second balloon 66b is inflated into the second largest size because the first balloon 66a is formed thinner than the second and third 66b and 66c and because the second balloon 66b is formed thinner than the third balloon 66c. The third balloon 66c is formed at the largest thickness and is therefore inflated less.

Next, a fourth embodiment will be described using FIGS. 8A and 8B. This embodiment is a modification of the first embodiment, so that the same signs are assigned to the same members as those described in the first embodiment, and these members are not described in detail.

Figure 8A:
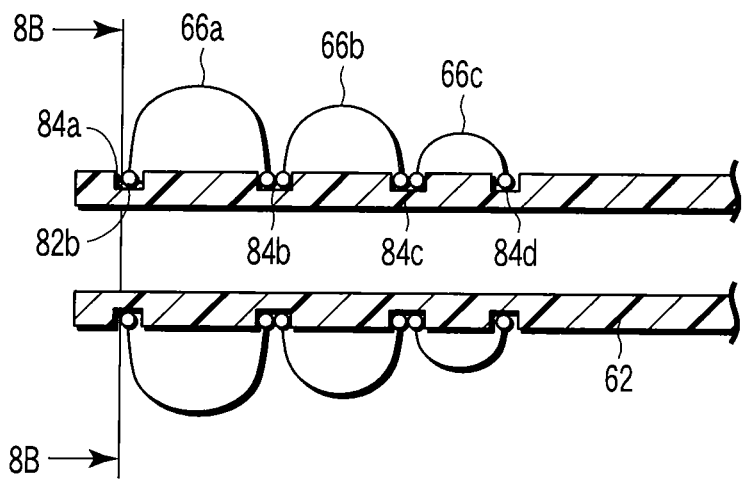
FIG. 8A is a schematic longitudinal sectional view showing the distal end of an overtube in an endoscopic system according to a fourth embodiment of the present invention.
Figure 8B:
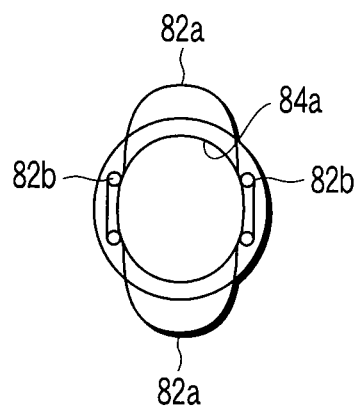
FIG. 8B is a schematic transverse sectional view along the 8B-8B line in FIG. 8A.

As shown in FIG. 8B, each of first to third balloons 66a, 66b and 66c includes a pair of bags 82a and a pair of bands 82b.

As shown in FIG. 8A, first to fourth grooves 84a, 84b, 84c and 84d are formed in the outer peripheral surface of a main body 62. The length $L_1$ between the first and second grooves 84a and 84b is formed to be larger than the length $L_2$ between the second and third grooves 84b and 84c. The length $L_2$ between the second and third grooves 84b and 84c is formed to be larger than the length $L_3$ between the third and fourth grooves 84c and 84d. In this case, the first balloon 66a is formed thinner than the second balloon 66b, and the second balloon 66b is formed thinner than the third balloon 66c.

Therefore, the times for inflating the first to third balloons 66a, 66b and 66c can be about the same. Then, it is possible to prevent, for example, any one of the first to third balloons 66a, 66b and 66c from being in an overpressurized state or a low pressure state.

Next, a modification of the fourth embodiment will be described using FIG. 8C.

Among the grooves 84a, 84b, 84c and 84d shown in FIG. 8A, the second groove 84b is used in common by the proximal side of the first balloon 66a and the distal side of the second balloon 66b. The third groove 84c is used in common by the proximal side of the second balloon and the distal side of the third balloon 66c.

Figure 8C:
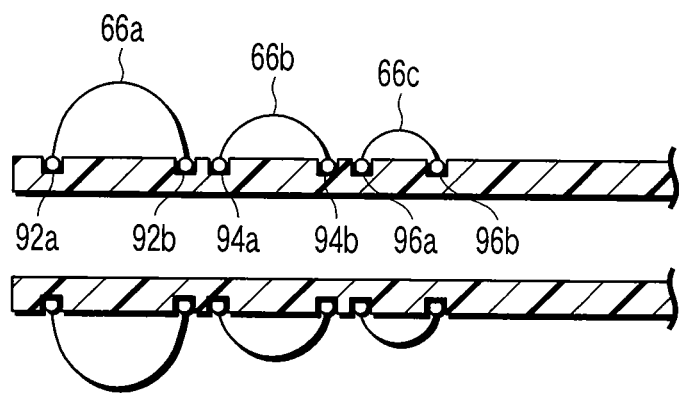
FIG. 8C is a schematic longitudinal sectional view showing the distal end of the overtube in the endoscopic system according to the fourth embodiment of the present invention.

Conversely, grooves 92a, 92b, 94a, 94b, 96a and 96b shown in FIG. 8C are separately provided. In this case, the positions of the balloons 66a, 66b and 66c can be suitably set. That is, the distance between the balloons 66a, 66b and 66c can be suitably set.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic insertion aid relative to a flexible tubular body having an inner wall, a tube member which includes a distal end having an outer periphery, a distal side and a proximal side, which is configured to be inserted into the tubular body and which is configured to receive therethrough an insertion section of an endoscope and to guide longitudinal movement of the insertion section; a pipeline which is provided in the tube member and which communicates with a supply/discharge unit to supply a fluid to the distal end of the tube member or discharge the fluid from the distal end of the tube member; a plurality of balloons which are disposed on the outer periphery of the distal end of the tube member and adjacently arranged longitudinally along the tube member, which communicate with the pipeline, which are configured to inflate/deflate in accordance with the supply/discharge of the fluid via the pipeline and which are configured to be inserted into the tubular body with the distal end of the tube member, positions of the plurality of balloons being configured to be held to the tubular body by frictional force between the balloons and the inner wall of the tubular body when the plurality of balloons are inflated; and a regulating portion configured to regulate inflation when the plurality of balloons is inflated so that the balloon disposed on the distal side of the tube member is inflated to have an outside diameter larger than an outside diameter of the balloon disposed closer to the proximal side of the tube member; wherein the balloon disposed on the distal side among the plurality of balloons is formed of a material having an expansion rate higher than that of the balloon disposed closer to the proximal side, each of two adjacent balloons among the plurality of balloons is configured to hook the inner wall of the tubular body therebetween when the plurality of balloons are inflated, and each of the plurality of balloons is configured to hook the inner wall of the tubular body by a proximal part thereof and configured to fold the tubular body when the plurality of balloons are inflated and the tube member is pulled relative to the tubular body, the insertion method comprising:

inserting the insertion section of the endoscope into the body cavity together with the tube member;

inflating the plurality of balloons to bring the plurality of balloons into close contact with the inside of the body cavity;

pulling the tube member and the insertion section of the endoscope to a proximal side of the tube member so that each of the plurality of balloons is in close contact with the inside of the body cavity and proximal part of the each of the plurality of balloons is in close contact with the inside of the body cavity and folds the body cavity; and advancing the insertion section with respect to the tube member.

2. The insertion method according to claim 1, further comprising:

bending the insertion section to advance the tube member along the insertion section of the endoscope after advancing the insertion section with respect to the tube member.

* * * * *